United States Patent
Hu et al.

(10) Patent No.: US 11,471,541 B2
(45) Date of Patent: Oct. 18, 2022

(54) USE OF MIR-21 IN PREPARATION OF DRUG FOR TREATING INTRAUTERINE ADHESION AND/OR THIN ENDOMETRIUM

(71) Applicant: NANJING DRUM TOWER HOSPITAL, Nanjing (CN)

(72) Inventors: Yali Hu, Nanjing (CN); Yan Zhou, Nanjing (CN); Guangfeng Zhao, Nanjing (CN); Ruotian Li, Nanjing (CN)

(73) Assignee: NANJING DRUM TOWER HOSPITAL, Nanjing (CN)

( * ) Notice: Subject to any disclaimer, the term of this patent is extended or adjusted under 35 U.S.C. 154(b) by 354 days.

(21) Appl. No.: 16/634,644

(22) PCT Filed: Feb. 23, 2018

(86) PCT No.: PCT/CN2018/077040
§ 371 (c)(1),
(2) Date: Jan. 28, 2020

(87) PCT Pub. No.: WO2019/071902
PCT Pub. Date: Apr. 18, 2019

(65) Prior Publication Data
US 2021/0085806 A1    Mar. 25, 2021

(30) Foreign Application Priority Data
Oct. 9, 2017 (CN) .......................... 201710929803.9

(51) Int. Cl.
*A61K 49/00* (2006.01)
*A61P 15/00* (2006.01)
*C12N 15/113* (2010.01)

(52) U.S. Cl.
CPC .......... *A61K 49/0054* (2013.01); *A61P 15/00* (2018.01); *C12N 15/113* (2013.01)

(58) Field of Classification Search
CPC .... A61K 49/0054; A61P 15/00; C12N 15/113
See application file for complete search history.

(56) References Cited

U.S. PATENT DOCUMENTS

2012/0107825 A1    5/2012 Winger et al.

FOREIGN PATENT DOCUMENTS

| | | |
|---|---|---|
| CN | 104039983 A | 9/2014 |
| CN | 106319031 A | 1/2017 |
| CN | 106367474 A | 2/2017 |
| CN | 107519194 A | 12/2017 |
| KR | 20170011588 A | 2/2017 |
| WO | 2017/041711 A1 | 3/2017 |

OTHER PUBLICATIONS

Chen, Ji-ming et al. "Role of MiR-21 mediated transforming growth factor-b signaling pathway in pathogenesis of endometriosis" Journal of Reproductive Medicine 23(11), pp. 927-931, 2014.
Liu, Xin et al. "Analysis of MicroRNA Species in Intrauterine Adhesion" Journal of Medical Research 43(8), pp. 171-174, 2014.
Liu, Yanmei et al. "The Research Development of MicroRNA in Fibrosis Diseases and Its Relationship with Diseases Caused by Intrauterine Adhesions" Medical Innovation of China 13(23), pp. 145-148, 2016.
Li, Jingxiong. "Study on the Impact Mechanism of TGF-b1/Smad Signaling Pathway in Intrauterine Adhesion Regulated by MicroRNA-29b" China Doctoral Dissertations Full-text Database, No. 7, 2017.
Jun. 22, 2018 International Search Report issued in International Patent Application No. PCT/CN2018/077040.

*Primary Examiner* — Robert S Cabral
(74) *Attorney, Agent, or Firm* — Oliff PLC

(57) ABSTRACT

Provided is use of miR-21 in preparation of a therapeutic drug or diagnostic reagent for intrauterine adhesion and/or thin endometrium.

9 Claims, 3 Drawing Sheets
Specification includes a Sequence Listing.

SEQUENCE LISTING

```
<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: probe sequence

<400> SEQUENCE: 1
ucaacaucag ucugauaagc ua                                            22

<210> SEQ ID NO 2
<211> LENGTH: 22
<212> TYPE: RNA
<213> ORGANISM: Human adenovirus type 1

<400> SEQUENCE: 2
uagcuuauca gacugauguu ga                                            22
```

USE OF MIR-21 IN PREPARATION OF DRUG FOR TREATING INTRAUTERINE ADHESION AND/OR THIN ENDOMETRIUM

BACKGROUND

Technical Field

The invention belongs to the field of biological pharmacy, and relates to use of miR-21 in preparation of a drug for treating intrauterine adhesion and/or thin endometrium.

Related Art

The endometrium regeneration disorders mainly include intrauterine adhesion and thin endometrium. Intrauterine adhesion is an adhesion between uterine walls characterized by endometrial fibrosis resulting from the damage to endometrial basal layer and the regeneration and repair disorders of a functional layer, which is the most common reason of uterine infertility, and accounts for up to 25-30% of patients with infertility. In China, with the increase of uterine cavity surgery, particularly painless induced abortion, the incidence rate of intrauterine adhesion and endometrial fibrosis is obviously increased. At present, the treatments mainly include separating adhesion by operation, and placing an intrauterine device, a saccule or biological materials for blocking the front wall and the rear wall of the uterus to prevent re-adhesion. However, these treatments have poor therapeutic efficacy against severe intrauterine adhesions, the incidence of re-adhesion is still as high as 62.5%, and endometrial fibrosis remains to be a serious obstacle for embryo implantation even if no re-adhesion. Thin endometrium refers to that the endometrial thickness of a patient is still not obviously increased after being stimulated with a large dose of estrogen, and such endometrium is called the thin endometrium. There is currently no wide consensus on the definition of thin endometrium thickness (generally considered as <7 mm). The effective treatment of intrauterine adhesion and thin endometrium is severely hampered by unclear pathogenesis. The present inventor finds in the research work that the thin endometrium in a large percentage of patients is also caused by uterine cavity surgery and that there is some degree of endometrial fibrosis. Therefore, there is an urgent need to find effective methods for predicting and treating intrauterine adhesion and thin endometrium.

miRNA is a class of endogenous, non-coding, small-molecule and single-stranded RNAs that are about 18-25 nucleotides in length and highly conserved across species. miRNA can regulate the expression of target genes by degrading target mRNA or inhibiting translation through an action mechanism of base matching. miR-21 is a miRNA located on a fragile site FRA17B of chromosome 17q23.2 and having an autonomous transcription unit. The expression of miR-21 in various tumor cells is remarkably abnormal, and the miR-21 participates in the regulation of the expression of various cancer suppressor genes and epithelial mesenchymal transition (EMT), suggesting that the miR-21 functions as a carcinogenic miRNA and plays an important role in the occurrence and metastasis of various tumors. In addition, miR-21 is remarkably and highly expressed in liver, kidney and lung fibrosis, suggesting that it promotes fibrosis. However, there is no report on whether miR-21 is related to the intrauterine adhesion syndrome or not, whether miR-21 affects endometrial fibrosis or not and the like.

SUMMARY

The object of the present invention is to provide use of miR-21 in preparation of a drug for treating intrauterine adhesion and/or thin endometrium.

Another object of the present invention is to provide use of miR-21 in preparation of a diagnostic reagent for treating intrauterine adhesion and/or thin endometrium.

The purpose of the invention is achieved by the following technical solution:

Use of miR-21 in preparation of a drug for treating intrauterine adhesion and/or thin endometrium.

Use of miR-21 in preparation of a drug for treating the diseases caused by intrauterine adhesion and/or thin endometrium.

The diseases caused by intrauterine adhesion and/or thin endometrium are preferably uterine infertility, recurrent abortion, and placenta adhesion and implantation caused by intrauterine adhesion and/or thin endometrium.

Use of miR-21 in preparation of a diagnostic reagent for intrauterine adhesion and/or thin endometrium.

Use of a reagent for detecting miR-21 in preparation of a diagnostic reagent for intrauterine adhesion and/or thin endometrium.

The reagent for detecting miR-21 preferably includes: PCR and qPCR primers, Taqman probes, digoxin or fluorescent dye-labeled probes, miRNA expression profile chips, and deep sequencing.

The sequence of the digoxin or fluorescent dye-labeled probes is further preferably: 5'ucaacaucagucugauaagcua3' (SEQ ID NO. 1).

Use of miR-21 in treatment of intrauterine adhesion and/or thin endometrium.

Use of miR-21 in treatment of diseases caused by intrauterine adhesion and/or thin endometrium; the diseases caused by endometrium regeneration disorders are preferably uterine infertility, recurrent abortion, and placenta adhesion and implantation caused by intrauterine adhesion and/or thin endometrium.

Use of a reagent for detecting miR-21 in diagnosis of intrauterine adhesion and/or thin endometrium.

The reagent for detecting miR-21 preferably includes: PCR and qPCR primers, Taqman probes, digoxin or fluorescent dye-labeled probes, miRNA expression profile chips, and deep sequencing. The sequence of miR-21 according to the present invention is: 5'uagcuuaucagacugauguuga3' (SEQ ID NO. 2).

The intrauterine adhesion according to the present invention refers to an adhesion between uterine walls characterized by endometrial fibrosis resulting from the damage to endometrial basal layer and the regeneration and repair disorders of a functional layer.

The thin endometrium according to the present invention refers to that the endometrial thickness cannot be obviously increased under estrogen stimulation, and generally refers to the endometrium having a thickness of less than 7 mm.

Advantageous Effects

It is found that the expression of miR-21 in endometrial epithelial cells and interstitial cells of patients with intrauterine adhesion is remarkably reduced, and particularly, the reduced expression in epithelial cell is most remarkable. The results in vitro show that miR-21 reverses EMT of endometrial epithelial cells, thereby inhibiting fibrosis. Therefore, miR-21 can play an important role in the treatment and diagnosis of intrauterine adhesion, and can be used for preparing drugs for the diagnosis and treatment of intrauterine adhesion or preparing drugs for the treatment of other diseases related to uterine fibrosis. The present inventor finds in the research work that the thin endometrium in a large percentage of patients is also caused by uterine cavity surgery and that there is some degree of endometrial fibrosis. miR-21 can reverse EMT of endometrial epithelial cells, thereby inhibiting fibrosis, so it is expected to be used to treat thin endometrium, especially thin endometrium caused by uterine cavity surgery.

Panels A-D are the expression of E-cadherin, fibrosis-related genes FN1, a-SMA, and Collagen I, respectively.

Figure 3:
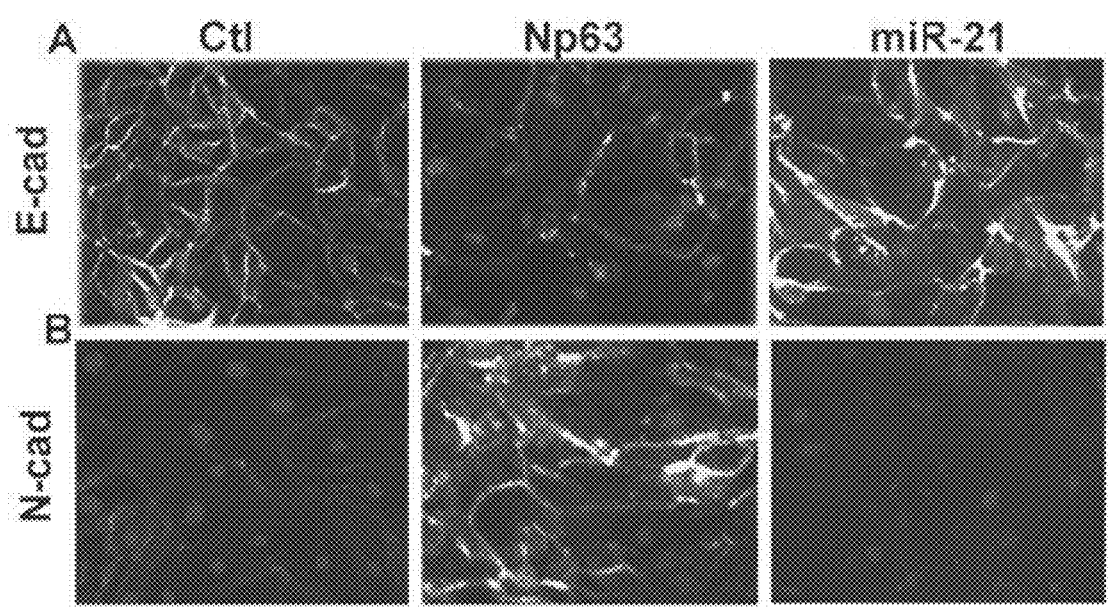

FIG. 3 is the effect of miR-21 on Np63-induced endometrial epithelial cell fibrosis.

Panel A shows the immunofluorescence results of E-cadherin; Panel B shows the immunofluorescence results of N-cadherin.

DETAILED DESCRIPTION

Example 1 Expression of miR-21 in Endometrial Tissues of Normal Patients and Patients with Severe Intrauterine Adhesion 1. Material, Reagent and Device
1.1 Source of Human Endometrial Tissue
5 normal endometrial tissues and 5 endometrial tissues of patients with severe intrauterine adhesion syndrome were collected. When the endometrial tissues were obtained, the size of follicles was detected by ultrasound to ensure that acquisition stages for the endometrial tissues were all late proliferation stages. All participants signed written informed consent form and the tests were approved by the Ethics Committee of Nanjing Drum Tower Hospital.
1.2 Primary Reagent
HASProbe™ MicroRNA in-situ detection probe (Pengekiphen biotechnology, Inc.), hybridization kit (Pengekiphen biotechnology, Inc.), Anti-Digoxigenin-AP (Roche), NBT/BCIP developer (Pengekiphen biotechnology, Inc.), xylene, ethanol, DEPC water, PBS, PFA, proteinase K, acetic anhydride, formamide, TEA, SSC, MAB, and Tween.
1.3 Primary Instrument
Hybridizer (Thermobrite), shaker, fluorescence microscope (Leica).
1.4 Primary Method
The expression of miR-21 was detected by adopting a paraffin section in-situ hybridization method. The section was treated twice with xylene, each for 15 min, treated with gradient of alcohol (100% ethanol for 5 min, 100% ethanol for 5 min, 95% ethanol for 3 min, 85% ethanol for 3 min, 70% ethanol for 3 min, and 30% ethanol for 3 min), and then washed with DEPC treated water for 3 min, and washed with 1×PBS for 3 min. After which, the section was treated with 4% PFA on ice for 10 min, and washed twice with 1×PBS, each for 5 min. After soaking with proteinase K at room temperature for 15 min, the section was washed with 1×PBS for 2 min. The section was rinsed with 1×TEA on a shaker for 10 min, and treated with 2×SSC for 5 min. After air drying, prehybridization was performed by incubating the section for 1 h, followed by hybridization overnight. The section was soaked with 1×SSC (containing 50% formamide+0.1% Tween 20) for 15 min, and soaked twice with 0.2×SSC (containing 50% formamide+0.1% Tween 20), each for 10 min. The section was treated twice with 1×MAB (containing 0.1% Tween 20) at room temperature, each for 10 min. The section was blocked with a blocking buffer at 37° C. for 30 min, and then antibody (Anti-DIG-antibody) was added and left overnight at 4° C. After elution, the section was treated with an NBT/BCIP developer, mounted, and then observed under a microscope and photographed.

Figure 1:
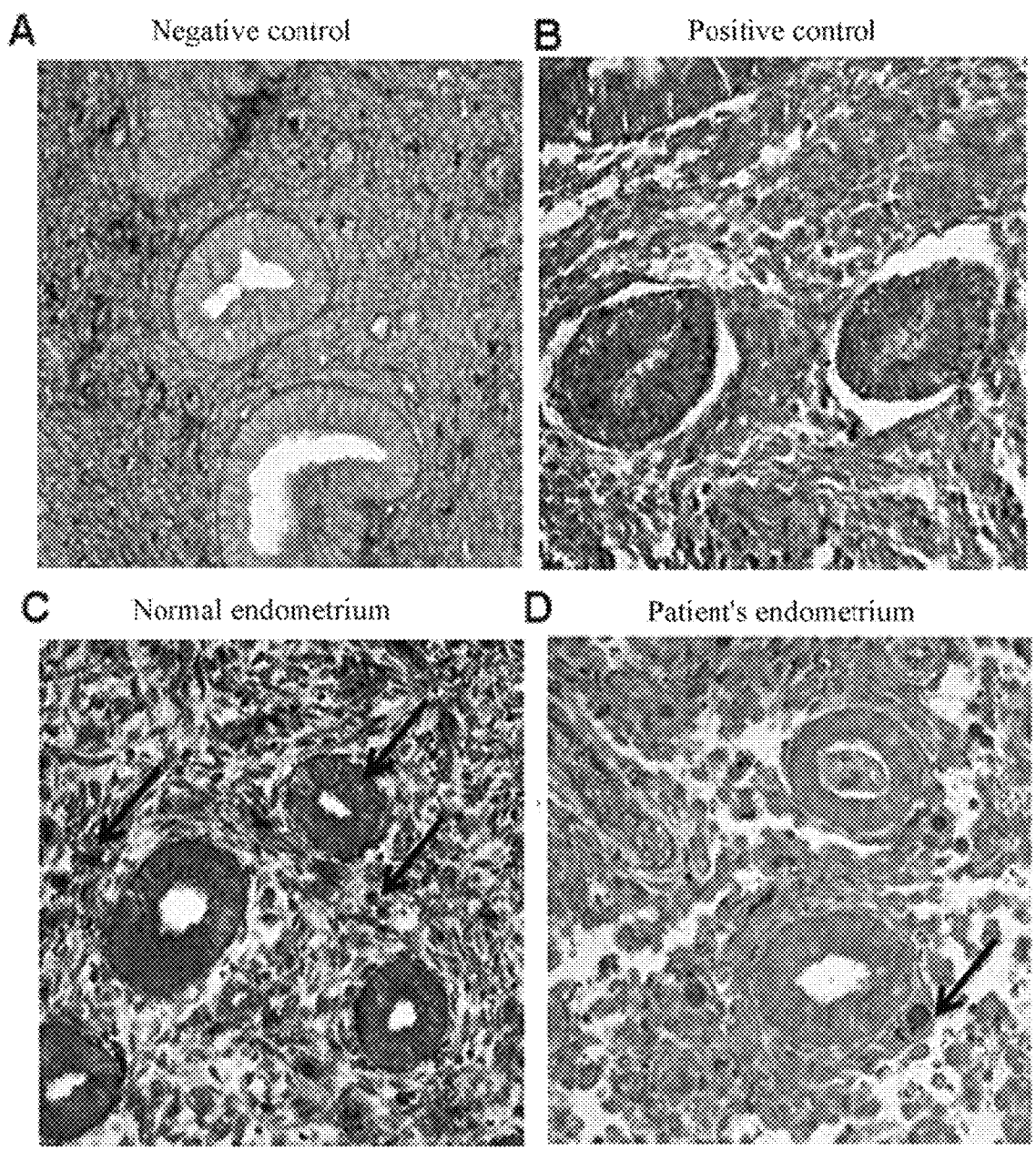
FIG. 1 is the analysis of miR-21 expression in endometrial tissues by in situ hybridization. A: miRNA negative control; B: miRNA positive expression control (miR-16); C: normal human endometrial miR-21 expression; D: endometrial miR-21 expression in a patient with intrauterine adhesion
Figure 2:
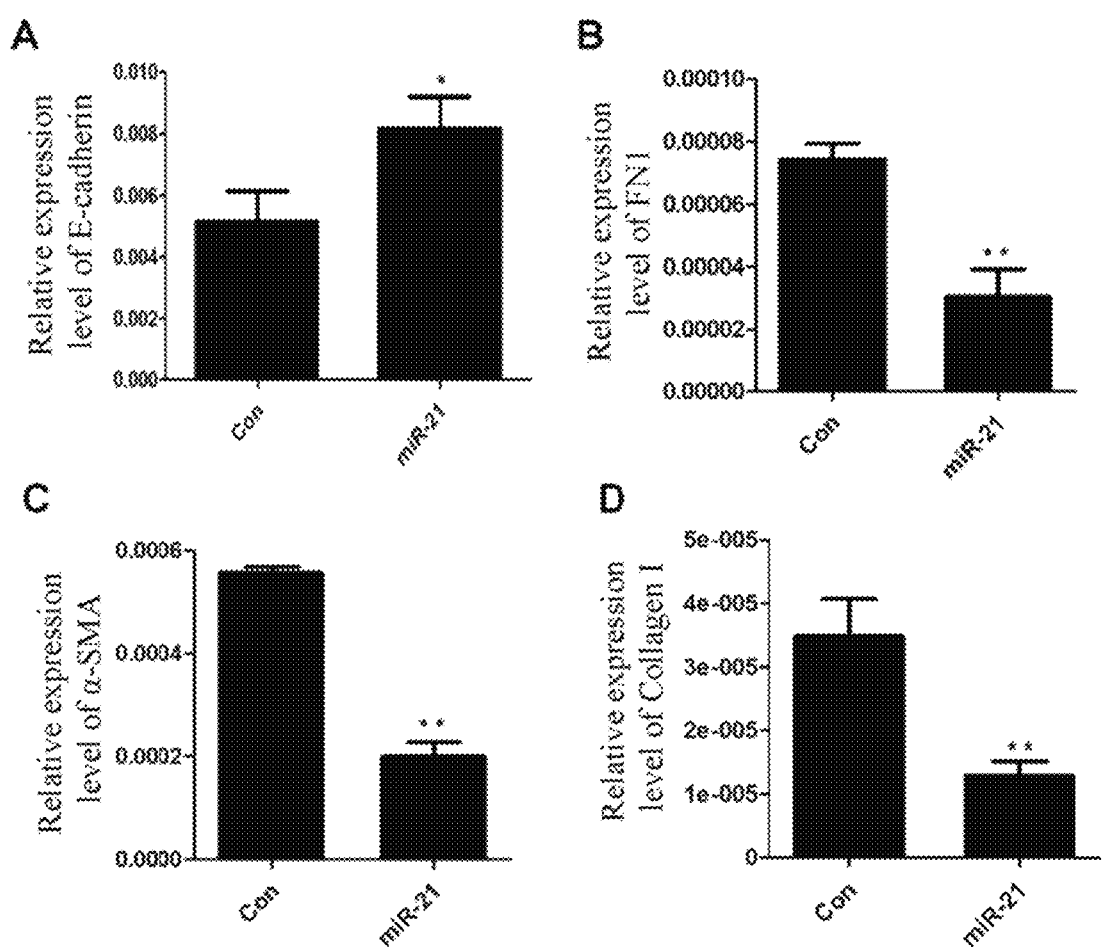
FIG. 2 is the effect of miR-21 on cell fibrosis-related gene expression.

2. Result
In the endometrial tissues of patients with severe intrauterine adhesion, the expression of miR-21 in epithelial cells and interstitial cells were all remarkably reduced, in which the reduced expression of miR-21 in the glandular epithelial cells was most remarkable (FIG. 1).

Example 2 Effect of miR-21 on Fibrosis of Endometrial Epithelial Cells

1. Material, Reagent and Device
1.1 Primary Reagents
Collagenase (Sigma), hyaluronidase (Sigma), DNAase (Roche), epithelial cell medium (Gibco), serum (Gibco), Trizol (Invitrogen), reverse transcriptase (Takara), qPCR enzyme (Roche).
1.2 Primary Instrument
Cell incubator, shaker, qPCR instrument (Roche), PCR instrument (ABI)
1.3 Primary Method
1.3.1 the Separation and Culture of Primary Endometrial Epithelial Cell
An endometrial tissue was placed in a fresh 60 mm culture dish, sheared until no visible block existed, a digestive juice prepared was added, the mixture was beaten and uniformly mixed, and placed in an incubator at 37° C. for 5 min; the culture dish was taken out, and the digestion condition was observed under a microscope; DNAase was added in a concentration of 4 mg/mL, and digestion was continued for 5 min; the digested tissue was blown and beaten and the tissue suspension was dropwise added onto a 40 μm sieve. The residual tissues in the sieve was transferred to a clean 35 mm culture dish, 2 ml of mixed solution of protease and collagenase was added, fully and uniformly mixed, and placed in an incubator at 37° C. for 5 min; whether the digested glandular tissue had been dispersed into single glands was observed under a microscope, and then an epithelial cell culture solution was added to stop digestion, and the glands were placed in a culture dish for culture.
1.3.2 RNA Extraction and Real-Time PCR
Total RNA was extracted by a Trizol method. 1 ug of RNA was reversely transcribed to obtain cDNA, which was diluted with RNase-free water in double volume and subjected to fluorescent quantitative PCR detection by an SYBRGreen method with 3 replicate wells per sample. The expression levels of different target genes were counted by using AACT values with GAPDH as an internal reference.

2. Result

After transfecting the endometrial epithelial cells with miR-21 for 48 h, the mRNA level of E-cadherin was remarkably increased, and the FN1, a-SMA and Collagen I gene expression were remarkably reduced, indicating that miR-21 inhibited the cell fibrosis process.

Example 3 Reversion of Np63-Induced Endometrial Epithelial Cell Fibrosis by miR-21

1. Material, Reagent, and Device
1.1 Primary Reagent
E-cadherin antibody (Abcam), N-cadherin antibody (Abcam), fluorescent secondary antibody (Jackson), DAPI-containing mountant (Abcam), PFA, antibody dilution (Gibco), methanol, Tween, and PBS.

1.2 Primary Instrument
Fluorescence microscope (Leica), shaker
1.3 Primary Method
The expression of E-cadherin and N-cadherin were detected by a cell immunofluorescence method. After sliding, the endometrial epithelial cells were infected with Np63 adenovirus for 24 h. A cell-loaded slide was then removed after transfecting with miR-21 for 48 h. The cells were washed with 1×PBS for 3 times, each for 5 min, and then fixed with PFA at room temperature for 15 min, washed with 1×PBS for 3 times, each for 5 min. The cells were treated with pre-chilled methanol for 5 min and washed with 1×PBS for 3 times, each for 5 min. After blocking with 2% BSA at room temperature for 1 h, E-cadherin and N-cadherin antibodies were added and left overnight at 4° C. The cells were then washed with PBST for 3 times, each for 5 min, the excessive primary antibody was thoroughly washed, and the water on a surface of the slide was blotted up after the last wash. A fluorescent secondary antibody was added dropwise, the mixture was incubated in an incubator at 37° C. for 30 min in the dark and washed with PBST for 3 times, each for 5 min, the water on the surface of the slide was blotted up after the last wash, DAPI dye containing an anti-quenching agent was dropwise added, observed under a fluorescent microscope and photographed in the dark.

2. Result
Np63 remarkably inhibited E-cadherin expression and promoted upregulation of N-cadherin expression. However, miR-21 promoted E-cadherin expression and reversed Np 63-induced upregulation of N-cadherin expression. The result showed that miR-21 had the effect of reversing fibrosis, and can be used for the treatment of the diseases caused by intrauterine adhesion and thin endometrium and/or uterine fibrosis, or the preparation of the drug for treating the diseases caused by intrauterine adhesion, thin endometrium and/or uterine fibrosis.

What is claimed is:

1. A method for treating intrauterine adhesion and/or thin endometrium, comprising increasing an amount of miR-21 in endometrial epithelial cells and/or interstitial cells so as to treat intrauterine adhesion and/or thin endometrium.

2. The method according to claim 1, wherein a therapeutically effective amount of miR-21 is provided to a subject in need of treatment for a disease caused by intrauterine adhesion and/or thin endometrium.

3. The method according to claim 2, wherein the disease is uterine infertility, recurrent abortion, or placenta adhesion and implantation caused by intrauterine adhesion and/or thin endometrium.

4. A method comprising detecting expression of miR-21 in a subject having or suspected of having intrauterine adhesion and/or thin endometrium with a reagent specific for miR-21.

5. A method for detecting intrauterine adhesion and/or thin endometrium, comprising performing the method according to claim 4 to measure whether there is underexpression of miR-21 in endometrial epithelial cells and/or interstitial cells.

6. The method according to claim 4, wherein the reagent is selected from the group consisting of PCR and qPCR primers, Taqman probes, digoxigenin or fluorescent dye-labeled probes, miRNA expression profile chips, and deep sequencing reagents.

7. The method according to claim 6, wherein the reagent comprises a digoxigenin or fluorescent dye-labeled probe that includes SEQ ID NO. 1.

8. The method according to claim 2, wherein the subject has intrauterine adhesion in which there is adhesion between uterine walls of the subject.

9. The method according to claim 2, wherein the subject has thin endometrium in which endometrial thickness is less than 7 mm.

* * * * *